(12) United States Patent  
Li

(10) Patent No.: US 12,396,637 B2
(45) Date of Patent: Aug. 26, 2025

(54) METHOD FOR MONITORING EYE STRAIN, ELECTRONIC DEVICE, AND STORAGE MEDIUM

(71) Applicants: Fu Tai Hua Industry (Shenzhen) Co., Ltd., Shenzhen (CN); HON HAI PRECISION INDUSTRY CO., LTD., New Taipei (TW)

(72) Inventor: Jun Li, Shenzhen (CN)

(73) Assignees: Fu Tai Hua Industry (Shenzhen) Co., Ltd., Shenzhen (CN); HON HAI PRECISION INDUSTRY CO., LTD., New Taipei (TW)

( * ) Notice: Subject to any disclaimer, the term of this patent is extended or adjusted under 35 U.S.C. 154(b) by 77 days.

(21) Appl. No.: 18/112,994

(22) Filed: Feb. 22, 2023

(65) Prior Publication Data

US 2024/0065542 A1 Feb. 29, 2024

(30) Foreign Application Priority Data

Aug. 30, 2022 (CN) .......................... 202211049730.1

(51) Int. Cl.
*A61B 3/10* (2006.01)
*A61B 5/00* (2006.01)
*A61B 5/01* (2006.01)
*G06T 7/12* (2017.01)
*G06T 7/62* (2017.01)
(Continued)

(52) U.S. Cl.
CPC ................ *A61B 3/10* (2013.01); *A61B 5/015* (2013.01); *A61B 5/4842* (2013.01); *G06T 7/12* (2017.01); *G06T 7/62* (2017.01); *G06T 7/68* (2017.01); *G06V 40/193* (2022.01); *G09G 5/10* (2013.01); *G16H 10/60* (2018.01); *G16H 40/67* (2018.01); *A61B 2560/0252* (2013.01); *G06T 2207/10048* (2013.01); *G06T 2207/30041* (2013.01); *G09G 2320/0626* (2013.01); *G09G 2354/00* (2013.01)

(58) Field of Classification Search
CPC ... A61B 2560/0252; A61B 3/10; A61B 3/113; A61B 5/015; A61B 5/4842; G09G 2320/0626; G09G 2354/00; G09G 5/10; G01J 2005/0077; G06T 2207/10024; G06T 2207/10048; G06T 2207/20104; G06T 2207/30041; G06T 2207/30201; G06T 7/62; G06T 7/68; G06T 7/0012; G16H 40/67; G16H 10/60; G16H 30/40; G16H 50/20; G06V 40/166; G06V 40/165; G06V 40/193; G06V 40/19; G06V 10/143
USPC .......................................................... 348/78
See application file for complete search history.

(56) References Cited

U.S. PATENT DOCUMENTS 7,027,621 B1 * 4/2006 Prokoski .............. G06V 40/165
340/576
11,806,078 B1 * 11/2023 Park ..................... A61B 3/0025
(Continued)

*Primary Examiner* — Peet Dhillon
(74) *Attorney, Agent, or Firm* — ScienBiziP, P.C.

(57) ABSTRACT

A method for monitoring eye strain implemented in an electronic device includes obtaining an infrared thermal image of eyes of a target user; analyzing the infrared thermal image of the eyes, and obtaining a temperature value of the eyes; monitoring whether the temperature value of the eyes is greater than a preset threshold of the eye temperature; and in response that the temperature value of the eyes is greater than the preset threshold of the eye temperature, outputting a prompt as to eye strain.

16 Claims, 3 Drawing Sheets

(51) Int. Cl.
*G06T 7/68* (2017.01)
*G06V 40/18* (2022.01)
*G09G 5/10* (2006.01)
*G16H 10/60* (2018.01)
*G16H 40/67* (2018.01)

(56) References Cited

U.S. PATENT DOCUMENTS

| | | | | |
|---|---|---|---|---|
| 2002/0049389 | A1* | 4/2002 | Abreu | A61B 3/0058 |
| | | | | 600/318 |
| 2005/0259849 | A1* | 11/2005 | Pavlidis | A61B 5/015 |
| | | | | 382/118 |
| 2006/0097176 | A1* | 5/2006 | Szu | G06T 7/0012 |
| | | | | 250/370.08 |
| 2006/0193498 | A1* | 8/2006 | Hartlove | G06V 40/103 |
| | | | | 374/E13.003 |
| 2013/0114043 | A1* | 5/2013 | Balan | H04N 13/344 |
| | | | | 351/210 |
| 2014/0313309 | A1* | 10/2014 | Matsuo | A61B 5/0077 |
| | | | | 348/78 |
| 2016/0080720 | A1* | 3/2016 | Fullam | A61B 3/14 |
| | | | | 345/156 |
| 2018/0161579 | A1* | 6/2018 | Franke | A61B 5/1127 |
| 2019/0336052 | A1* | 11/2019 | Baker | G01N 21/35 |
| 2021/0156749 | A1* | 5/2021 | Tewolde | G06T 5/50 |
| 2021/0321876 | A1* | 10/2021 | Zare Bidaki | A61B 5/0077 |
| 2022/0020149 | A1* | 1/2022 | Mian | G06T 7/0012 |
| 2022/0240779 | A1* | 8/2022 | Peyman | A61B 5/1176 |
| 2023/0036164 | A1* | 2/2023 | Lee | G06N 3/09 |
| 2023/0043342 | A1* | 2/2023 | Tremblay | H04N 23/698 |

* cited by examiner

METHOD FOR MONITORING EYE STRAIN, ELECTRONIC DEVICE, AND STORAGE MEDIUM

FIELD

The subject matter herein generally relates to a technology of smart display, and particularly to an electronic device, a method for monitoring eye strain, and a storage medium.

BACKGROUND

A user can often be watching a monitor for a longer time, which may cause eye strain, and is not healthy. The eye strain is usually monitored according to a time taken per unit of eyes-closed time in proportion to time passing, as a preset percentage. However, eyes are commonly already in a fatigued state but the user does not close his eyes. Eye strain monitored in this way is not accurate and unreliable regarding timely warnings.

BRIEF DESCRIPTION OF THE DRAWINGS

Many aspects of the disclosure can be better understood with reference to the following drawings. The components in the drawings are not necessarily drawn to scale, the emphasis instead being placed upon clearly illustrating the principles of the disclosure. Moreover, in the drawings, like reference numerals designate corresponding parts throughout the several views.

DETAILED DESCRIPTION

Figure 1:
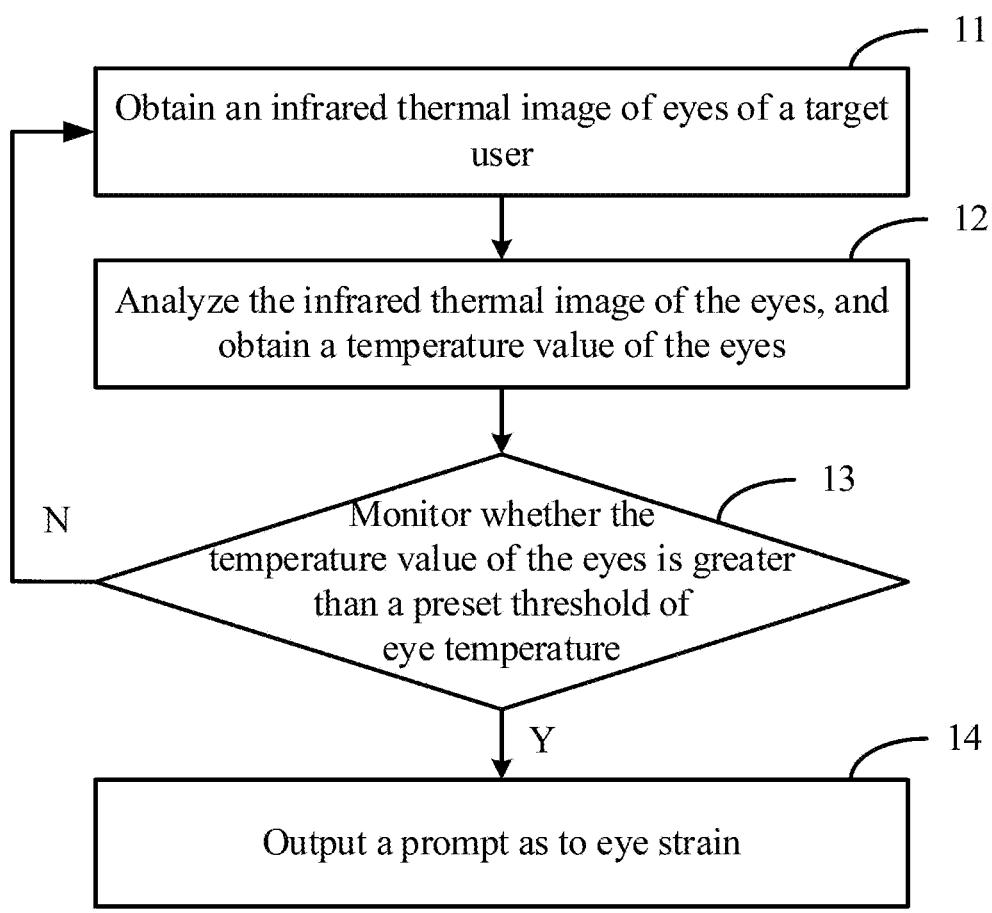
FIG. 1 illustrates a flowchart of an embodiment of a method for monitoring eye strain according to the present disclosure.

Multiple embodiments are described in the present disclosure, but the description is exemplary rather than limiting, and there may be more embodiments and implementation solutions within the scope of the embodiments described in the present disclosure. Although many possible combinations of features are shown in the drawings and discussed in the detailed description, many other combinations of the disclosed features are also possible. Unless specifically limited, any feature or element of any embodiment may be used in combination with or in place of any other feature or element of any other embodiment.

When describing representative embodiments, the specification may present methods and/or processes as a specific sequence of steps. However, to the extent that the method or process does not depend on the specific order of steps described in the present disclosure, the method or process should not be limited to the specific order of steps described. As understood by those of ordinary skills in the art, other orders of steps are also possible. Therefore, the specific order of steps set forth in the specification should not be interpreted as a limitation to the claims. In addition, the claims for the method and/or process should not be limited to the steps performed in the written order, and those skilled in the art may readily understand that these orders may vary and still remain within the essence and scope of the embodiments of the present disclosure.

Unless otherwise defined, technical terms or scientific terms used in the embodiments shall have common meanings as understood by those of ordinary skills in the art to which the present disclosure pertains. The terms "first", "second" and the like used in the embodiments of the present disclosure do not represent any order, quantity, or importance, but are merely used to distinguish different components. The terms "include", "contain" or the like do not mean that other elements or articles are excluded. The terms "connect", "link" or the like are not limited to physical or mechanical connection, but may include electrical connections, whether direct or indirect.

In order to allow eye strain or potential eye strain of the user to be monitored timely and accurately, an infrared thermal image of the eye of the user is obtained, in this embodiment. The infrared thermal image is analyzed and the eye temperature is obtained to determine whether the user has the eye strain, providing timely and accurate monitoring of the eye condition of the user.

A method for monitoring eye strain is applied to an electronic device. The electronic device can be a head-mounted device (e.g., a head-mounted display device, glasses, etc.), or other smart device, such as a personal computer, a tablet computer, a smart phone, a digital camera, a smart wearable device (e.g., a watch, a wristband, etc.), a smart car meter, a smart TV, etc.

FIG. 1 illustrates a flowchart of an embodiment of a method for monitoring eye strain. The method is provided by way of example, as there are a variety of ways to carry out the method. Each block shown in FIG. 1 represents one or more processes, methods, or subroutines carried out in the example method. Furthermore, the illustrated order of blocks is by example only and the order of the blocks can be changed. Additional blocks may be added or fewer blocks may be utilized, without departing from this disclosure. The example method can begin at block 11.

At block 11, obtaining an infrared thermal image of eyes of a target user.

In one embodiment, the target user is a user who needs to be monitored for eye strain when using an electronic device. The infrared thermal image of the eyes is an image indicating the temperature of the eyes. Each pixel in the infrared thermal image of the eyes carries temperature information. The infrared thermal image of the eyes can be obtained by an image acquisition device in the electronic device, and the image acquisition device can be a camera, which is not limited.

In one embodiment, the electronic device includes a display device and the image acquisition device, the display device presents images or data for the user to watch, the image acquisition device is used to capture the infrared thermal image of the eyes of the target user, and the electronic device is also provided with relevant modules for eye strain analysis based on the infrared thermal image of the eyes. In one embodiment, the relevant modules may include an image analysis module and a temperature monitoring module. The image analysis module is used to analyze the infrared thermal image of the eyes, and obtain a temperature value of the eyes. The temperature monitoring module is used to monitor whether the temperature value of the eyes is greater than a preset threshold of eye temperature, and when the temperature value of the eyes is greater than the preset threshold of eye temperature, it is determined that the user has the eye strain; when the temperature value of the eyes is equal to or less than the preset threshold, it is determined that the user does not have the eye strain.

When the electronic device is a head-mounted device, the head-mounted device may be glasses, or a head-mounted display device, etc. The head-mounted device includes a display device and an image acquisition device, and the display device presents data for the user to watch, the image acquisition device is used to capture the infrared thermal image of the eyes of the target user, and the head-mounted device is further provided with relevant modules for performing eye strain analysis based on the infrared thermal image of the eyes. In one embodiment, the relevant modules may include an image analysis module and a temperature monitoring module. The image analysis module is used to analyze the infrared thermal image of the eyes, and obtain the temperature value of the eyes. The temperature monitoring module is used to monitor whether the temperature value of the eyes is greater than the preset threshold of eye temperature, and when the temperature value of the eyes is greater than the preset threshold of eye temperature, it is determined that the user has eye strain; when the temperature value of the eyes is equal to or less than the preset threshold, it is determined that the user does not have eye strain.

Taking the head-mounted device as glasses as an example, in one embodiment, the glasses include a frame, a display device arranged in the frame, connecting blocks symmetrically arranged on both sides of the frame, and two legs of glasses. Each leg is hinged on an end surface that is away from the frame of each connecting block. The display device is watched by the user, the image acquisition device is arranged in the frame and captures the infrared thermal image of the eyes of the target user, and the glasses is further provided with relevant modules for performing eye strain analysis based on the infrared thermal image of the eyes. In one embodiment, the relevant module for performing eye strain analysis based on the infrared thermal image of the eyes may be arranged in the legs of the glasses.

It can be understood that in other embodiments, the glasses may include or not include the frame, may be rimless glasses, and the shape of the glasses is not limited.

It can be understood that, in other embodiments, the relevant modules for performing eye strain analysis based on the infrared thermal image of the eyes may also be set according to the specific shape of the glasses, which is not limited. In this embodiment, the infrared thermal image of the eyes of the target user is obtained by the head-mounted device, and the eye strain analysis is performed based on the infrared thermal image of the eyes, so that the eye condition of the user can be monitored timely and accurately, and eyesight can be protected against deterioration.

In another embodiment, when the electronic device is a smart device, such as a smart phone, a computer, a tablet, a smart TV, a meter of a smart car, a smart watch, or a wristband, the smart device can include the display device and the image capture device, the display device presents data for the user to watch, the image acquisition device is used to capture an infrared thermal image of the eyes of the target user, and the smart device is also provided with relevant modules for eye strain analysis based on the infrared thermal image of the eyes.

In detail, the image acquisition device obtains an infrared thermal image of a face of the target user, the infrared thermal image of the face includes the infrared thermal image of the eyes. The smart device is further provided with relevant modules for eye strain analysis based on the infrared thermal image of the face, the infrared thermal image of the eyes is obtained by locating a position of the eyes in the infrared thermal image of the face, the eye temperature is analyzed to monitor the eye strain according to the infrared thermal image of the eyes. In one embodiment, the relevant modules may include an eye locating module, the image analysis module, and the temperature monitoring module. The eye locating module obtains the infrared thermal image of the eyes by locating the position of the eyes in the infrared thermal image of the face. The image analysis module is used to analyze the infrared thermal image of the eyes, and obtain the temperature value of the eyes. The temperature monitoring module is used to monitor whether the temperature value of the eyes is greater than the preset threshold of eye temperature, and when the temperature value of the eyes is greater than the preset threshold of eye temperature, it is determined that the user has the eye strain; when the temperature value of the eyes is equal to or less than the preset threshold of eye temperature, it is determined that the user does not have the eye strain.

In this embodiment, the infrared thermal image of the eyes of the target user is obtained by the smart device, and the eye strain analysis is performed based on the infrared thermal image of the eyes, so that the eye condition of the user can be monitored timely and accurately, and eyesight can be protected against deterioration.

In one embodiment, before obtaining the infrared thermal image of the eyes of the target user, the method further includes: obtaining an infrared thermal image of a face of the target user; performing a histogram equalization process on the infrared thermal image of the face, and obtaining a first facial infrared thermal image; performing a binarization process on the first facial infrared thermal image, and obtaining a contour line of a facial area corresponding to the first facial infrared thermal image; determining a target facial area according to the contour line of the facial area, and determining a position of the eyes in the target facial area.

In one embodiment, the histogram equalization is a simple and effective image space domain enhancement technology, which can change the histogram of the image mainly by modifying the grayscale value of each pixel in the image, to improve the contrast of the image with too restricted grayscale dynamic range. The histogram indicates the distribution of grayscale values at all levels in the original image, and expresses the overall description of all grayscale values in an image. If the grayscale values of the original image are concentrated in a relatively small range, it will result in poor image definition. For example, when the exposure is insufficient, the grayscale values of the image are concentrated in the low-brightness range, and when it is overexposed, the grayscale values of the image are mainly concentrated in the high-brightness range. The histogram equalization is used to perform grayscale transformation on the original image, and the grayscale values of the image pixels are redistributed, so that the grayscale levels in the image are more uniformly distributed over the entirety. The dynamic range of the grayscale differences between pixels can thus be enlarged, so as to achieve the effect of enhancing the overall contrast of the image. The facial infrared thermal image is processed by the using histogram equalization, and the edge detection and enhancement on the image are performed. Binarization process is performed on the first facial infrared thermal image to obtain the contour line of the facial area corresponding to the first facial infrared thermal image, and an area within the contour line of the facial area is the target facial area. The target facial area refers to an area including facial features, and the target facial area includes features such as the eyes, the forehead, and the mouth etc.

In one embodiment, determining a position of the eyes in the target facial area includes: performing a binarization process on the target facial area, and obtaining eye information and mouth information corresponding to the target facial area; determining a triangular relationship between the eye information and the mouth information; determining the position of the eyes by a preset symmetry axis algorithm according to the triangular relationship.

In one embodiment, there is a triangular relationship between the eye information and the mouth information, and the preset symmetry axis algorithm may be a symmetry axis method of the eyes and the face. The embodiment adopts the symmetry axis method of the eyes and the face to accurately locate the eyes even under different postures and facial expressions of the target user.

In one embodiment, a preset time interval may be set, and the infrared thermal image of the eyes is periodically obtained according to the preset time interval. In one embodiment, the preset time interval may be preset, such as five minutes. In another embodiment, historical eyestrain data of the target user may also be obtained in advance, and the time interval at which the temperature value of the eyes of the target user reaches a preset threshold of the eye temperature is obtained, by analyzing the historical eyestrain data, the infrared thermal image of the eyes of the target user is obtained according to the obtained time interval. In the embodiment, the energy consumption of the electronic device can be reduced by setting the time interval for obtaining the infrared thermal image of the eyes.

In one embodiment, obtaining the infrared thermal image of the eyes of the target user includes: obtaining historical eyestrain data corresponding to the target user; inputting the historical eyestrain data into a preset mathematical model, and obtaining the time interval at which the temperature value of the eyes of the target user reaches the preset threshold of the eye temperature; determining the time interval to be the preset time interval, and obtaining the infrared thermal image of the eyes according to the preset time interval.

In one embodiment, the historical eyestrain data includes a number of initial time intervals when the eye temperature of the users reaches the preset threshold of the eye temperature each time that the user uses the electronic device, and the number of the initial time intervals is the same as the number of times the electronic device is used, which is not limited. The preset mathematical model can be a mean value calculation model, that is, the preset mathematical model calculates the mean value of the number of initial time intervals, the mean value is the time interval when the temperature value of the eyes of the target user reaches the preset threshold of the eye temperature. In one embodiment, the historical eyestrain data corresponding to the target user can be obtained by means of identity identification, and the means of identity identification may include face recognition, fingerprint recognition, voiceprint recognition, account login, etc., which are not limited.

In one embodiment, obtaining historical eyestrain data corresponding to the target user includes: obtaining the identity of the target user; obtaining a preset mapping relationship between the identity and the historical eyestrain data; traversing the preset mapping relationship, and obtaining the historical eyestrain data of the target user corresponding to the identity of the target user.

In one embodiment, the identity may be an identity including face information, fingerprint information, voiceprint information, account information, etc., which are not limited.

At block 12, analyzing the infrared thermal image of the eyes, and obtaining a temperature value of the eyes.

In one embodiment, analyzing the infrared thermal image of the eyes, and obtaining a temperature value of the eyes includes: obtaining a pixel point set of the infrared thermal image of the eyes; determining the temperature value corresponding to each pixel point in the pixel point set, and obtaining a temperature value set; processing the temperature values in the temperature value set by calling up a preset function, and obtaining the temperature value of the eyes.

In one embodiment, the preset function can be a preset function for performing a data process on the temperature values of the temperature value set. In one embodiment, the preset function may be an overall mean value calculation function, processing the temperature values in the temperature value set by calling up a preset function, and obtaining the eye temperature value, these processes include: calculating the mean value of the temperature values in the temperature value set, and determining the mean value to be the temperature value of the eyes.

In one embodiment, processing the temperature values in the temperature value set by calling up a preset function, and obtaining the temperature value of the eyes includes: obtaining all temperature values in the temperature value set; calculating a mean value of all the temperature values, and obtaining the temperature value of the eyes.

In other embodiments, the preset function may also be a function for obtaining a local mean value, and processing the temperature values in the temperature value set by calling up a preset function, and obtaining the temperature value of the eyes includes: obtaining temperature values of a target area in the temperature value set, calculating the mean value of the temperature values of the target area, and determining the mean value to be the temperature value of the eyes.

In another embodiment, processing the temperature values in the temperature value set by calling up a preset function, and obtaining the temperature value of the eyes further includes: determining a target area of the infrared thermal image of the eyes; determining an area vector corresponding to each temperature value in the temperature value set, and determining the temperature values of the area vector within a range of the target area as being target temperature values; calculating a mean value of the target temperature values, and obtaining the temperature value of the eyes.

In one embodiment, the target area may be a pupil area, and the target area may be obtained by determining the area vectors corresponding to the pupil part, which is not limited.

At block 13, monitoring whether the temperature value of the eyes is greater than a preset threshold of the eye temperature, and if the temperature value of the eyes is greater than the preset threshold of the eye temperature, the process goes to block 14.

In one embodiment, for different environment information, the threshold of the eye temperature when the eyes is fatigued may fluctuate. The environment information refers to the environment in which the user uses the electronic device, and the environment information may include environment temperature and environment humidity. In one embodiment, the environment temperature can be monitored by a temperature sensor, and the environment humidity can be monitored by a humidity sensor.

For example, when the user uses the electronic device outdoors under a high temperature, the target threshold of the eye temperature may be increased by an eye temperature floating value based on the initial threshold of the eye temperature, such as an increase of 2.2 degrees Celsius;

when the user uses the electronic device in the air-conditioned room, the target threshold of the eye temperature may be increased by another eye temperature floating value, such as an increase of 1.5 degrees Celsius, on the basis of the initial threshold of the eye temperature. The initial threshold of the eye temperature can be a preset threshold, and the eye temperature floating value can be set according to the environment information.

In one embodiment, before monitoring whether the temperature value of the eyes is greater than a preset threshold of the eye temperature, the method further includes: obtaining an initial threshold of the eye temperature; obtaining the environment information in which the target user locates, and determining the eye temperature floating value according to the environment information; adjusting the initial threshold of the eye temperature according to the eye temperature floating value, and obtaining the preset threshold of the eye temperature.

In one embodiment, there is a mapping relationship between the environment information and the eye temperature floating value. Based on the obtained environment information, the eye temperature floating value corresponding to the environment information can be obtained by querying the mapping relationship. Adjusting the initial threshold of the eye temperature according to the eye temperature floating value, and obtaining the preset threshold of the eye temperature includes adding or subtracting the eye temperature floating value on the basis of the initial threshold of the eye temperature, and obtaining the target threshold of the eye temperature.

In one embodiment, when the temperature value of the eyes is equal to or less than the target threshold of the eye temperature, it is determined that the target user does not have eye strain.

At block 14, outputting a prompt as to the eye strain.

In one embodiment, the prompt can be output by means of text messages, phone calls, emails, voice broadcasts, vibrations, etc., which is not limited. The prompt is used to prompt that the user is suffering the eye strain.

In other embodiments, after outputting the prompt as to the eye strain, if the target user being monitored continues to use the electronic device, the screen brightness of the electronic device is required to be adjusted as a prompt to the target user to rest.

In one embodiment, after outputting the prompt as to the eye strain, the method further includes: obtaining a current temperature difference between the temperature value of the eyes and the preset threshold of the eye temperature; traversing a preset relationship between the temperature differences and the degrees of eye strain according to the current temperature difference, and obtaining the degree of eye strain corresponding to the current temperature difference; adjusting the brightness of the display screen of the electronic device according to the degree of eye strain.

In one embodiment, the temperature difference between the temperature value of the eyes and the preset threshold of the eye temperature can indicate the degree of eye strain of the target user, and the degrees of eye strain includes slight strain, moderate strain, and deep strain from low to high. It can be understood that, the larger the temperature difference, the heavier the eye strain the target user has. The preset relationship is pre-established between the temperature differences and the degrees of eye strain, and the degree of eye strain corresponding to the temperature difference can be obtained by traversing the preset relationship according to the current temperature difference.

In one embodiment, adjusting the brightness of the display screen of the electronic device according to the degree of eye strain includes: obtaining a preset relationship between the degrees of eye strain and the brightness of the display screen; traversing the preset relationship between the degrees of eye strain and the brightness of the display screen, and obtaining the target brightness of the display screen corresponding to the degree of eye strain; adjusting the current brightness of the display screen to the target brightness.

For example, when the target user has the slight strain, the brightness of the display screen can be adjusted to 80% of the original level; when the target user has the moderate strain, the brightness of the display screen can be adjusted to 50% of the original level; when the target user has the deep strain, the brightness of the display screen can be turned off, that is, the display screen of the electronic device is turned off.

The embodiment provides a method for monitoring eye strain, by obtaining the infrared thermal image of the eyes of a target user, and analyzing the infrared thermal image of the eyes to obtain the temperature value of the eyes, so as to determine whether the target user has the eye strain. The accurate and timely monitoring of the strain condition of the eyes of the user is thus improved.

Figure 2:
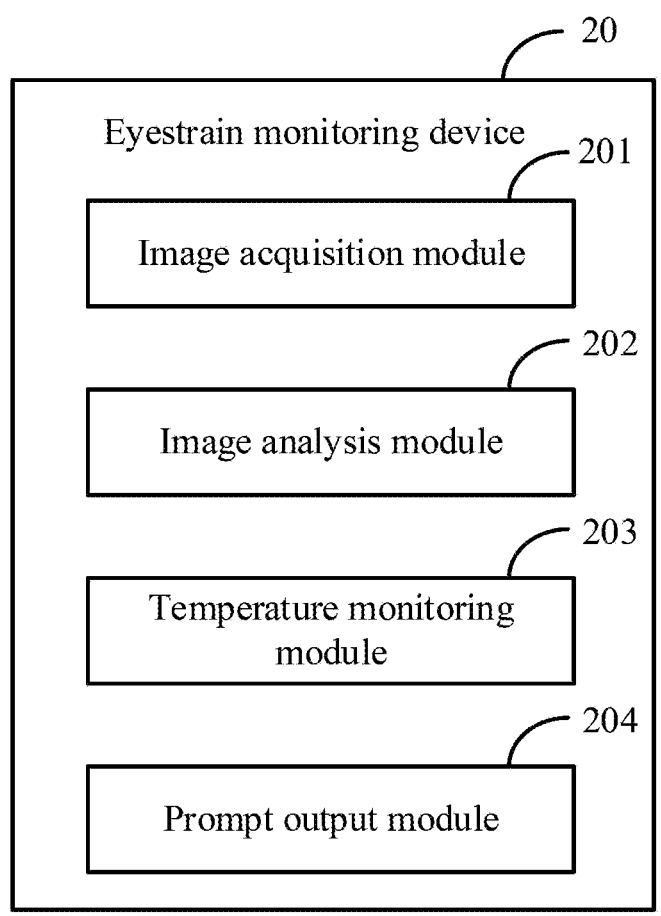
FIG. 2 is a block diagram of an embodiment of an eye strain monitoring device according to the present disclosure.

Referring to FIG. 2, an eyestrain monitoring device 20 is provided. The eyestrain monitoring device 20 may include a number of functional modules according to the functions performed by the eyestrain monitoring device 20. The functional modules may include: an image acquisition module 201, an image analysis module 202, a temperature monitoring module 203, and a prompt output module 204. The module referred to in this application refers to a series of computer program segments that can be executed by at least one processor and can perform preset functions, and are stored in a memory. In this embodiment, the function of each module will be described in detail.

The image acquisition module 201 is used to acquire an infrared thermal image of the eyes of the target user.

The image analysis module 202 is used to analyze the infrared thermal image of the eyes to obtain the temperature value of the eyes.

The temperature monitoring module 203 is used to monitor whether the temperature value of the eyes is greater than a preset threshold of the eye temperature.

The prompt output module 204 is used to output a prompt as to eye strain when the temperature value of the eyes is greater than the preset threshold of the eye temperature.

Figure 3:
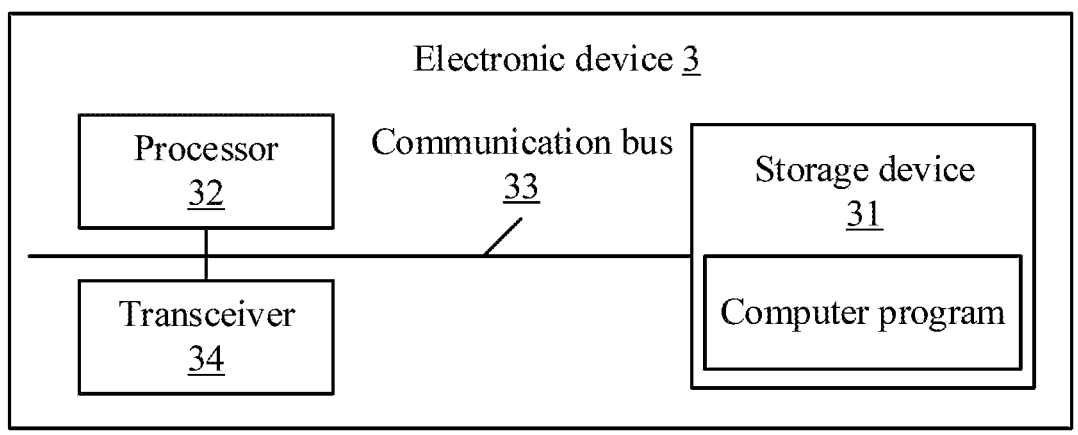
FIG. 3 is a block diagram of an embodiment of an electronic device according to the present disclosure.

FIG. 3 illustrates an electronic device 3 in one embodiment. The electronic device 3 includes, but is not limited to, a storage device 31, a processor 32, at least one communication bus 33, and a transceiver 34. FIG. 3 illustrates only one example of the electronic device 3. Other examples can include more or fewer components than as illustrated or have a different configuration of the various components in other embodiments.

The processor 32 can be a central processing unit (CPU), a microprocessor, or other data processor chip that performs functions in the electronic device 3.

In one embodiment, the storage device 31 can include various types of non-transitory computer-readable storage mediums. For example, the storage device 31 can be an internal storage system, such as a flash memory, a random access memory (RAM) for the temporary storage of information, and/or a read-only memory (ROM) for permanent storage of information. The storage device 31 can also be an external storage system, such as a hard disk, a storage card, or a data storage medium.

The storage device 31 stores instructions, and the processor 32 executes the computer program 30 stored in the storage device 31 for implementing the method for monitoring eye strain provided in the embodiments of the present disclosure. The computer program can be an eyestrain monitoring program and can include instructions.

Upon execution of the instructions stores in the storage device 31, the processor 32 is configured to:
obtain an infrared thermal image of eyes of a target user;
analyze the infrared thermal image of the eyes, and obtain a temperature value of the eyes;
monitor whether the temperature value of the eyes is greater than a preset threshold of the eye temperature;
output a prompt as to the eye strain, when the temperature value of the eyes is greater than the preset threshold of the eye temperature.

It is believed that the present embodiments and their advantages will be understood from the foregoing description, and it will be apparent that various changes may be made thereto without departing from the spirit and scope of the disclosure or sacrificing all of its material advantages, the examples hereinbefore described merely being embodiments of the present disclosure.

What is claimed is:

1. A method for monitoring eye strain implemented in an electronic device comprising:
obtaining an infrared thermal image of eyes of a target user;
analyzing the infrared thermal image of the eyes, and obtaining a temperature value of the eyes;
obtaining an initial threshold of the eye temperature;
obtaining environment information in which the target user locates, and determining a floating value of the eye temperature according to the environment information;
adjusting the initial threshold of the eye temperature according to the floating value of the eye temperature, and obtaining a preset threshold of the eye temperature;
monitoring whether the temperature value of the eyes is greater than the preset threshold of eye temperature;
in response that the temperature value of the eyes is greater than the preset threshold of the eye temperature, outputting a prompt as to eye strain;
obtaining a current temperature difference between the temperature value of the eyes and the preset threshold of eye temperature;
traversing a preset relationship between temperature differences and degrees of eye strain according to the current temperature difference, and obtaining a degree of eye strain corresponding to the current temperature difference; and
adjusting brightness of a display screen of the electronic device according to the degree of eye strain.

2. The method according to claim 1, wherein analyzing the infrared thermal image of the eyes, and obtaining a temperature value of the eyes comprises:
obtaining a pixel point set of the infrared thermal image of the eyes;
determining a temperature value corresponding to each pixel point in the pixel point set, and obtaining a temperature value set comprising a plurality of temperature values; and
processing the plurality of temperature values in the temperature value set by calling up a preset function, and obtaining the temperature value of the eyes.

3. The method according to claim 2, wherein processing the plurality of temperature values in the temperature value set by calling up a preset function, and obtaining the temperature value of the eyes comprises:
calculating a mean value of the plurality of temperature values in the temperature value set; and
determining the mean value to be the temperature value of the eyes.

4. The method according to claim 2, wherein processing the plurality of temperature values in the temperature value set by calling up a preset function, and obtaining the temperature value of the eyes further comprises:
determining a target area of the infrared thermal image of the eyes;
determining an area vector corresponding to each of the plurality of temperature values in the temperature value set, and determining temperature values of the area vectors within a range of the target area to be a plurality of target temperature value; and
calculating a mean value of the plurality of target temperature values, and determining the mean value to be the temperature value of the eyes.

5. The method according to claim 1, wherein obtaining an infrared thermal image of eyes of a target user comprises:
obtaining historical data of eye strain corresponding to the target user;
inputting the historical data of eye strain into a preset mathematical model, and obtaining a time interval at which the temperature value of the eyes of the target user reaches a preset threshold of eye temperature; and
determining the time interval to be a preset time interval, and obtaining the infrared thermal image of the eyes according to the preset time interval.

6. The method according to claim 5, wherein obtaining historical data of eye strain corresponding to the target user comprises:
obtaining an identity of the target user;
obtaining a preset mapping relationship between the identities of users and the historical data of eye strain; and
traversing the preset mapping relationship, and obtaining the historical data of eye strain of the target user corresponding to the identity of the target user.

7. The method according to claim 1, wherein adjusting brightness of a display screen of the electronic device according to the degree of eye strain comprises:
obtaining a preset relationship between the degree of eye strain and the brightness of the display screen;
traversing the preset relationship between the degree of eye strain and the brightness of the display screen, and obtaining target brightness of the display screen corresponding to the degree of eye strain; and
adjusting current brightness of the display screen to the target screen brightness.

8. The method according to claim 1, further comprising:
obtaining an infrared thermal image of a face of the target user;
performing a histogram equalization process on the infrared thermal image of the face, and obtaining a first facial infrared thermal image;
performing a binarization process on the first facial infrared thermal image, and obtaining a contour line of a facial area of the first facial infrared thermal image; and
determining a target facial area according to the contour line of the facial area, and determining a position of the eyes in the target facial area.

9. The method according to claim 8, wherein determining a position of the eyes in the target facial area comprises:

performing the binarization process on the target facial area, and obtaining eye information and mouth information of the target facial area;

determining a triangular relationship between the eye information and the mouth information; and determining the position of the eyes by a preset symmetry axis algorithm according to the triangular relationship.

10. An electronic device comprising:

at least one processor; and a storage device coupled to the at least one processor and storing instructions for execution by the at least one processor to cause the at least one processor to:

obtain an infrared thermal image of eyes of a target user;

analyze the infrared thermal image of the eyes, and obtain a temperature value of the eyes;

obtain an initial threshold of the eye temperature;

obtain environment information in which the target user locates, and determine a floating value of the eye temperature according to the environment information;

adjust the initial threshold of the eye temperature according to the floating value of the eye temperature, and obtain a preset threshold of the eye temperature;

monitor whether the temperature value of the eyes is greater than the preset threshold of eye temperature;

in response that the temperature value of the eyes is greater than the preset threshold of the eye temperature, output a prompt as to eye strain;

obtain a current temperature difference between the temperature value of the eyes and the preset threshold of eye temperature;

traverse a preset relationship between temperature difference and the degrees of eye strain according to the current temperature difference, and obtain a degree of eye strain corresponding to the current temperature difference; and adjust brightness of a display screen of the electronic device according to the degree of eye strain.

11. The electronic device according to claim 10, wherein the at least one processor is further caused to:

obtain a pixel point set of the infrared thermal image of the eyes;

determine a temperature value corresponding to each pixel point in the pixel point set, and obtain a temperature value set comprising a plurality of temperature values; and process the plurality of temperature values in the temperature value set by calling up a preset function, and obtain the temperature value of the eyes.

12. The electronic device according to claim 11, wherein the at least one processor is further caused to:

calculate a mean value of the plurality of temperature values in the temperature value set; and determine the mean value to be the temperature value of the eyes.

13. The electronic device according to claim 11, wherein the at least one processor is further caused to:

determine a target area of the infrared thermal image of the eyes;

determine an area vector corresponding to each of the plurality of temperature values in the temperature value set, and determine temperature values of the area vectors within a range of the target area to be a plurality of target temperature value; and calculate a mean value of the plurality of target temperature values, and determine the mean value to be the temperature value of the eyes.

14. The electronic device according to claim 10, wherein the at least one processor is further caused to:

obtain historical data of eye strain corresponding to the target user;

input the historical data of eye strain into a preset mathematical model, and obtain a time interval at which the temperature value of the eyes of the target user reaches a preset threshold of eye temperature; and determine the time interval to be a preset time interval, and obtain the infrared thermal image of the eyes according to the preset time interval.

15. The electronic device according to claim 14, wherein the at least one processor is further caused to:

obtain an identity of the target user;

obtain a preset mapping relationship between the identities of users and historical data of eye strain; and traverse the preset mapping relationship, and obtain the historical data of eye strain of the target user corresponding to the identity of the target user.

16. A non-transitory computer-readable storage medium having instructions stored thereon, when the instructions are executed by a processor of an electronic device, the processor is configured to perform a method for monitoring eye strain, wherein the method comprises:

obtaining an infrared thermal image of eyes of a target user;

analyzing the infrared thermal image of the eyes, and obtaining a temperature value of the eyes;

obtaining an initial threshold of the eye temperature;

obtaining environment information in which the target user locates, and determining a floating value of the eye temperature according to the environment information;

adjusting the initial threshold of the eye temperature according to the floating value of the eye temperature, and obtaining a preset threshold of the eye temperature;

monitoring whether the temperature value of the eyes is greater than the preset threshold of eye temperature;

in response that the temperature value of the eyes is greater than the preset threshold of the eye temperature, outputting an eye strain prompt;

obtaining a current temperature difference between the temperature value of the eyes and the preset threshold of eye temperature;

traversing a preset relationship between temperature differences and degrees of eye strain according to the current temperature difference, and obtaining a degree of eye strain corresponding to the current temperature difference; and adjusting brightness of a display screen of the electronic device according to the degree of eye strain.

* * * * *